United States Patent
Remington et al.

(10) Patent No.: US 7,108,862 B2
(45) Date of Patent: *Sep. 19, 2006

(54) BONE GROWTH COMPOSITIONS AND METHODS

(75) Inventors: Benjamin J. Remington, Modesto, CA (US); David J. Bearss, Modesto, CA (US); Kavian Shahi, Granite Bay, CA (US)

(73) Assignee: Neuropro Technologies, Inc., Modesto, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 10/460,645

(22) Filed: Jun. 11, 2003

(65) Prior Publication Data

US 2004/0006125 A1    Jan. 8, 2004

Related U.S. Application Data

(63) Continuation-in-part of application No. 10/282,338, filed on Oct. 28, 2002, now Pat. No. 7,041,309.

(60) Provisional application No. 60/394,791, filed on Jul. 10, 2002, provisional application No. 60/388,222, filed on Jun. 13, 2002.

(51) Int. Cl.
*A61F 2/28* (2006.01)

(52) U.S. Cl. ............... 424/426; 424/423; 424/424; 424/425; 424/426; 523/113; 523/116

(58) Field of Classification Search ............ 424/423, 424/424, 425, 426; 623/16.11, 17.11; 523/113, 523/116

See application file for complete search history.

(56) References Cited

U.S. PATENT DOCUMENTS

| | | | |
|---|---|---|---|
| 4,870,063 A | 9/1989 | Binderup et al. |
| 5,258,376 A | 11/1993 | Bernstein |
| 5,280,040 A | 1/1994 | Labroo et al. |
| 5,336,687 A | 8/1994 | Sabatucci |
| 5,403,829 A | 4/1995 | Lehtinen et al. |
| 5,462,932 A | 10/1995 | Brenner et al. |
| 5,545,661 A | 8/1996 | Cullinan |
| 5,604,257 A | 2/1997 | Tabe et al. |
| 5,935,607 A | 8/1999 | Silver |
| 6,022,887 A | 2/2000 | Gasper et al. |
| 6,040,334 A | 3/2000 | Myers et al. |

(Continued)

FOREIGN PATENT DOCUMENTS

WO    WO03105731    * 12/2003

OTHER PUBLICATIONS

Wozney, J. M., et al. Engineering What Comes Naturally—Tissue engineers have developed a synthetic matrix that interacts with host cells to deliver bone-inductive proteins for bone regeneration. Nature Biotechnology. May 2003. vol. 21: 506-508.

(Continued)

*Primary Examiner*—Carlos A. Azpuru
(74) *Attorney, Agent, or Firm*—Wilson Sonsini Goodrich & Rosati

(57) ABSTRACT

The present invention provides an improved technique for spinal fusion involving the administration of an HMG-CoA reductase inhibitor to a fusion. The HMG-CoA reductase inhibitor is preferably delivered to the site by a carrier. More preferably, the HMG-CoA reductase inhibitor is delivered to the site by a non-compressible delivery vehicle. The invention is suitable for promoting non-anatomic or heterotopic bone growth between any bony surfaces where bone growth is desired but does not naturally occur.

57 Claims, 11 Drawing Sheets

U.S. PATENT DOCUMENTS

| | | |
|---|---|---|
| 6,080,779 A | 6/2000 | Gasper et al. |
| 6,083,690 A | 7/2000 | Harris et al. |
| 6,153,212 A | 11/2000 | Mao et al. |
| 6,207,153 B1 | 3/2001 | Dan et al. |
| 6,322,797 B1 | 11/2001 | Mao et al. |
| 6,369,109 B1 | 4/2002 | Debatin et al. |
| 6,376,476 B1 | 4/2002 | Gasper et al. |
| 6,376,644 B1 | 4/2002 | Mao et al. |
| 6,403,637 B1 | 6/2002 | Partridge |
| 6,462,019 B1 | 10/2002 | Mundy et al. |

OTHER PUBLICATIONS

Cook-Swartz Doppler Flow Probe and Monitoring System. Instructions for Use. 1998. Cook Vascular Incorporated. FM-1588C Apr. 2002.

* cited by examiner

BONE GROWTH COMPOSITIONS AND METHODS

CROSS REFERENCE TO RELATED APPLICATIONS

This application is a continuation-in-part of U.S. application Ser. No. 10/282,338, filed Oct. 28, 2002 now U.S. Pat. No. 7,041,309, which claims benefit of priority to Provisional Application No. 60/388,222, filed Jun. 13, 2002, and Provisional Application No. 60/394,791, filed Jul. 10, 2002. These applications are hereby incorporated by reference in their entirety.

SUMMARY OF THE INVENTION

The present invention relates to growth of non-anatomic or heterotopic bone. In one embodiment, HMG-CoA reductase inhibitors are used to stimulate non-anatomic bone growth in spinal fusion surgery. Preferably, the HMG-CoA reductase inhibitors are administered directly to the site of fusion. More preferably, the HMG-CoA reductase inhibitors are administered via a carrier, such as an open cell matrix. The carrier can further comprise of other therapeutic agents such as antibiotics, painkillers, antioxidants, growth factors, and timed release agent.

In another embodiment, the present invention involves the use of HMG-CoA reductase inhibitor to promote bone growth and fusion between any two bones. Bone fusion is effective in treatment post-traumatic, degenerative and/or inflammatory arthritis conditions. In one embodiment, the HMG-CoA reductase inhibitor is used in podiatric surgery, such as to immobilize the metatarsals or the ankle joint. Furthermore, HMG-CoA reductase inhibitors can be utilized in facial plastic and reconstruction surgeries, such as to fix the maxillary and mandibular bones, increase cheekbone morphology, and cranial vault fixation and remodeling (e.g., due to craniosynostosis).

The present invention further discloses instrumentations and implants that are coated or comprise of HMG-CoA reductase inhibitors which can be used for purposes of enhancing non-anatomic bone growth.

DETAILED DESCRIPTION OF THE INVENTION

Figure 1:
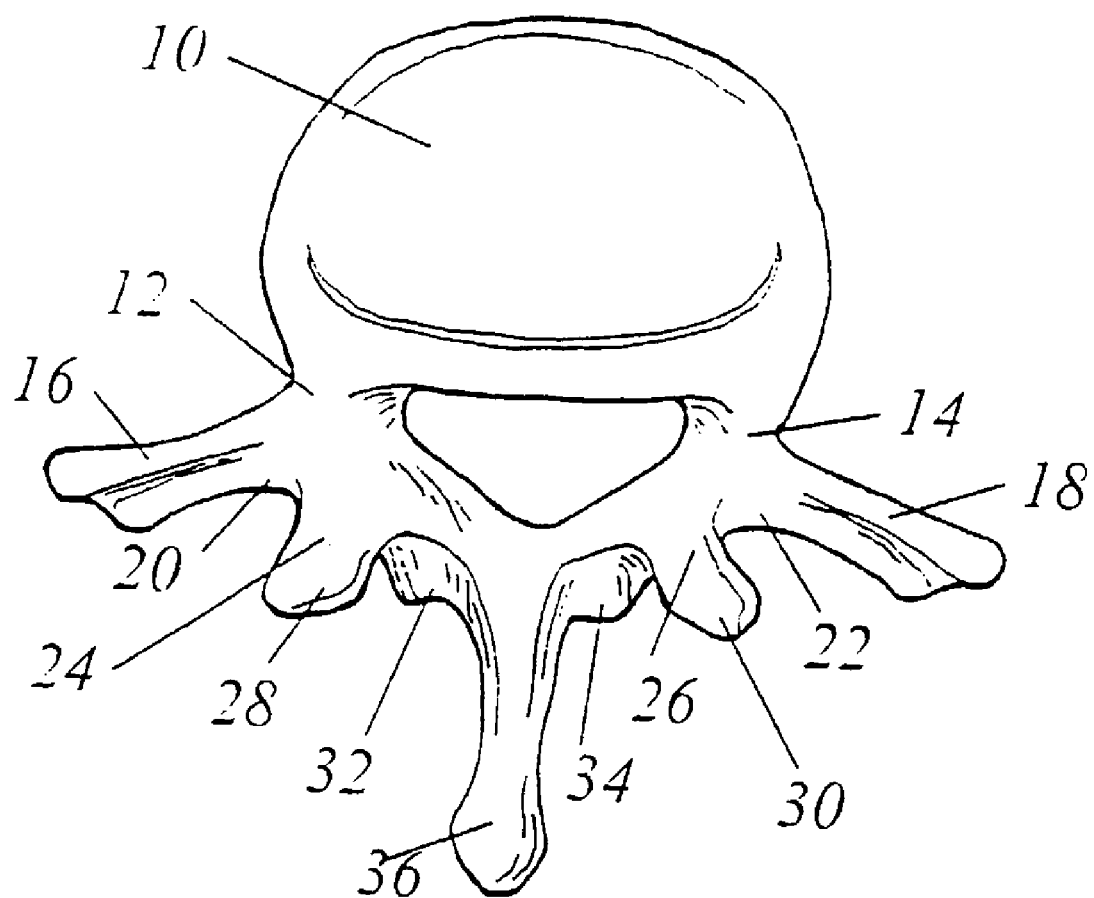
FIG. 1 is a superior view of a $2^{nd}$ lumbar vertebra.

The vertebrae are bones that make up the spinal column, which surrounds and protects the spinal cord. At each level in the spinal cord, there is a disc space in the front and paired facet joints in the back. Working together, these structures define a motion segment and permit multiple degrees of motion. Nerves from the spinal cord exit the spinal column between each vertebra. Intervertebral discs are soft tissues positioned between each vertebra. The discs act as cushions between the vertebrae by absorbing energy while the spinal column flexes, extends, and twists.

The disc allows for movements of the vertebrae and allows people bend and rotate their neck and back. The type and degree of motion varies between the different levels of the spine: cervical (neck), thoracic (chest) or lumbar (low back). The cervical spine permits movement in all directions. The thoracic spine protects the heart and lungs and is more rigid than the cervical spine due to rib presence. The lumbar spine permits primarily forward and backward bending movements, flexion and extension.

In spinal fusion, one or more vertebrae, vertebral segments or combination thereof, are fused to prevent any motion there between. There are many potential reasons for spinal fusion. Exemplary reasons include treatment of a fractured vertebra, correction of deformity, elimination of pain from painful motion, treatment of instability and treatment of cervical disc herniations. Some spinal fractures, including those associated with spinal cord or nerve injury, generally, require fusion as part of the surgical treatment. While not all spinal fractures require surgery, some fractures, including those associated with spinal cord or nerve injury, generally require fusion as part of the surgical treatment. In spondylolisthesis, a hairline fracture allows vertebrae to slip forward on top of each other. This condition may be treated by fusion surgery. Spinal fusion may also be used to correct certain types of spinal deformity such as scoliosis. Another condition treated with fusion surgery is actual or potential instability (or abnormal or excessive motion between two or more vertebrae). Cervical disc herniations requiring surgery often require fusion as well as removal of the herniated disc (discectomy). With this procedure, the disc is removed through an incision in the front of the neck (anteriorly) and a small piece of bone is inserted in place of the disc. Although disc removal is commonly combined with fusion in the neck, this is not generally the case in the lumbar spine. Further, spinal fusion may be required for the treatment of a painful spinal condition without clear instability.

There are numerous surgical approaches and methods for performing spinal fusion. Many of these approaches involve placement of a bone graft between the vertebrae to be fused. The spine may be approached and the graft placed either from the back (posterior approach), from the front (anterior approach) or by a combination of both approaches. The type and location of the incision for access to the spinal region depends on the area needing treatment. The lower spinal vertebrae are repaired through an incision directly over the spine (posterior lumbar approach). The upper spinal vertebrae are repaired through an incision in the back or side of the neck (cervical spine). The middle spinal vertebrae are repaired through an incision made in the chest and abdomen (anterior thoracic spine). The abnormal or injured vertebrae are repaired and stabilized with bone grafts, metal rods, other instrumentation, or a combination of the above.

The most common types of spinal fusion include posterolateral gutter fusion, posterior lumbar interbody fusion (PLIF), anterior lumbar interbody fusion (ALIF), anterior/posterior spinal fusion, cervical fusion, thoracic fusion, and interlaminar fusion.

Posterolateral gutter fusion involves placing bone graft in the posterolateral portion of the spine (a region just outside the spine). The surgical approach to this spinal fusion is from the back through a midline incision that is approximately three inches to six inches long. Typically, bone graft is obtained from the pelvis (the iliac crest) and the harvested bone graft is laid out in the posterolateral portion of the spine. The back muscles that attach to the transverse processes are elevated to support the bone graft. The back muscles are replaced over the bone graft to create tension to hold the bone graft in place. After surgery, the body attempts to heal itself by growing bone. The growth of bone by the body grows the harvested bone graft and adheres the graft to the transverse processes. At this point, spinal fusion is achieved and motion at that segment is stopped.

Posterior lumbar interbody fusion (PLIF) involves adding bone graft to an area of the spine to set up a biological response that causes bone to grow between the two vertebrae and stop the motion at that segment. PLIF achieves spinal fusion by inserting bone graft directly into the disc space. The spine is approached through an incision (typically three to six inches long) in the midline of the back and the left and right erector spinae are stripped off the lamina on both sides and at multiple levels. After the spine is approached, the lamina is removed (laminectomy) to allow visualization of the nerve roots. The facet joints, which are directly over the nerve roots, are trimmed to make more space for the nerve roots. The nerve roots are retracted to one side and the disc space is cleaned of the disc material. A bone graft, or interbody cage with bone, or other instrumentation or implant, is inserted into the disc space and the bone grows from vertebral body to vertebral body.

Anterior lumbar interbody fusion (ALIF) is similar to the PLIF, except that in ALIF the disc space is fused by approaching the spine through the abdomen instead of through the back. In the ALIF approach, an incision (typically three to five inches) is made on the left side of the abdomen and the abdominal muscles are retracted to the side. The peritoneum can also be retracted to allow the surgeon access to the front of the spine. Some ALIF procedures are done using a minilaparotomy (one small incision) or with an endoscope (a scope that allows the surgery to be done through several one-inch incisions). Regardless of the specific procedure, the aorta and vena cava are moved aside, the disc material is removed and bone graft, or bone graft and anterior interbody cages, other implant, or instrumentation, is inserted.

Anterior/posterior lumbar fusion involves performing a lumbar interbody fusion and a posterolateral gutter fusion to fuse both the front and back of the spine. Fusing both the front and back provides a high degree of stability for the spine and a large surface area for the bone fusion to occur. The disc may be approached either as an ALIF or as a PLIF, and the back part of the spine is fused with a posterolateral gutter fusion.

The neck is the upper portion of the spine and is made up of the seven upper vertebrae which are often referred to as the cervical spine. Numerous cervical spine disorders require surgery for relief of painful symptoms. One of the basic underlying factors associated with most spine disorders is the dehydration of the disks. Herniated cervical disk is a common neck pain diagnosis which results when the center of the nucleus bulges through the annulus and presses on a nerve, resulting in neck or arm pain, or weakness in the arm. Cervical fusion involves the stabilization of two or more vertebrae by locking them together. One can approach the cervical spine through a small incision in the front of the neck, usually within a skin fold line under the chin. After retracting neck muscles, the affected intervertebral disk is removed. This is called decompression. After removal, a bone graft may be inserted into the intervertebral region to fuse the upper and lower vertebrae together.

In many embodiments, spinal fusion involves the use of an implant to an area of the spine, usually between two vertebrae. An implant can be, for example, a compressible carrier (e.g., absorbable carrier such open cell matrix) or a non-compressible carrier (e.g., an instrumentation). Implants come in many shapes, sizes and materials. An implant can include membranes, films, plates, foam, mesh plates, screws, taps or other formed pieces to be implanted in the body. Implants can be used to support or attach tissue/bone, separate tissue/bone from other tissue/bone, serve as a time-release vehicle, etc. Implants can be made from a variety of compounds. An implant is preferably resorbable and composed of a polymer such as, polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides (e.g., cellulose, starch, dextran, chitin, chitosan, etc.), modified proteins (e.g., collagen, casein, fibrin, etc.) and their copolymers, or combinations thereof. Other polymers include polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), polydioxanone and copolymers, and polymer blends thereof.

In a preferred embodiment, a compressible carrier is a matrix, such as an open cell matrix. Preferably an open cell matrix comprises of collagen fibers. More preferably, such collagen fibers are coated with resorbable apatite, such as hydroxyapatite.

Non-compressible carriers such as surgical instrumentations can be used as an adjunct to obtain a solid fusion or provide stability. Surgical instrumentation can be fabricated from titanium and/or alloys of titanium, stainless steel, ceramic materials or rigid polymeric materials. Typical medical instrumentations include, for example, rods, hooks, braided cable, plates, screws, and threaded interbody cages. Instrumentation can decrease the likelihood of non-union by maintaining spinal stability while facilitating the process of fusion. For example, instrumentation can be used to bridge space created by the removal of a spinal element such as an intervertebral disc. Instrumentation can also be used to correct a deformity or as an internal splint to hold the vertebrae together while the bone grafts heal. In a preferred embodiment, an instrument is coated with synthetic apatites, or preferably hydroxyapatite. Unfortunately, even with the use of instrumentation, non-union remains a common problem.

Regardless of whether instrumentation or implants are used, bone or bone substitutes are preferably used to prompt the vertebrae to fuse together. Traditionally, the surgical technique includes a grafting procedure utilizing autologous bone harvested from a separate site. In a typical procedure, bone chips from a patient's pelvic bone are transplanted, or grafted, to the spinal vertebrae to help fusion there between. Alternatively, allograft, bone harvested from a bone bank or other source, may be used. Similarly, synthetic and xenograft derived bone substitutes (calcium phosphate, hydroxylapatite, and/or other ceramic based bone substitutes) may be used.

To function as a suitable bone graft for spinal fusion, a graft must have three characteristics. It must provide a source of primitive osteoprogenitor cells that form osteoblasts and osteocytes (osteopromotion). The graft material must produce local growth factors to stimulate bone growth and vascularity in the area (osteoinduction). Lastly, it must act as a scaffold to bone ingrowth (osteoconduction).

Although the use of autologous bone for spinal fusion is common, harvesting bone graft from a patient's body has many disadvantages. Among other things, graft harvesting prolongs surgical time, increases blood loss, increases the risk of infection, and can be a source of chronic pain. Significantly, use of autologous bone does not always ensure successful fusion, even when used in combination with instrumentation. Inherent limitations in autogenous and allogeneic bone grafting have led to exploration of other technology, for example, using bone morphogenic protein (BMP) in spinal fusion. As an adjuvant to allograft or as a replacement for harvested autograft, BMP can improve spinal fusion.

Bone growth and differentiation factors can be obtained in a variety of ways for application directly to a surgical site, including extraction of the factors from animal or human bone matrix, production of a single factor by cellular hosts by using recombinant technology, and direct delivery to cells at the site of desired bone formation of the DNA encoding for the factor. In particular, bone morphogenic proteins (BMPs), have been found to have an ability to stimulate formation of cartilage and bone in vivo.

BMPs have a multifaceted osteoinductive role, acting as chemotactic agents, growth factors and differentiation factors. As chemotactic factors, they can initiate the recruitment of progenitor and stem cells toward the area of bone injury. As growth factors, they can stimulate both angiogenesis and proliferation of stem cells from surrounding mesenchymal tissues. As differentiation factors, they can promote maturation of stem cells into chondrocytes, osteoblasts and osteocytes.

More specifically, BMPs can repair, regenerate and promote the growth and differentiation of bone in various parts of the skeleton. Thus, BMPs are extremely beneficial to patients undergoing bone fusion and/or augmentation procedures (e.g., spinal fusion) by eliminating the need for bone transplantation or bone grafting. Furthermore, several studies reveal that improved results of bone fusion and stability can be achieved using recombinant human BMP-2 in various carriers as compared to autologous bone grafts. See Pilitsis, J. G., *Neurosurg. Focus*, (2000) 13 (6).

There are some disadvantages to using BMPs for promotion of bone growth. As BMPs are expressed in a large variety of tissues, receptors for the BMPs have numerous temporal and spatial patterns throughout the body. This suggests that BMPs may have effects on many tissues in addition to bone and their usefulness as therapeutic agents, particularly when administered systemically, may be limited. There is also some concern regarding the local administration of BMPs to a surgical site, as it may be difficult to control BMPs effect on the surrounding tissue. The effects of BMPs in spinal fusion sites are particularly concerning as hypergrowth at or near the spine may pinch nerves and result in not only pain but also possibly paralysis. Consequently, it may not be desirable to apply BMP directly to a spinal fusion site.

The present invention relates generally to the administration of HMG-CoA reductase inhibitors (statins), or prodrugs thereof or a pharmaceutically acceptable salt of such statins or prodrug thereof to promote non-anatomical, or heterotopic, bone growth.

The terms "non-anatomic" and "heterotopic" bone growths refer to the generation of bone in regions that naturally do not grow bone.

The term "HMG-CoA reductase inhibitors" or "statins" as used herein refers to compounds that inhibit the enzyme 3-hydroxy-3-methylglutaryl coenzyme A (HMG-CoA) reductase. HMG-CoA reductase is the principal rate-limiting enzyme involved in cellular cholesterol biosynthesis. The pathway is also responsible for the production of dolichol, ubiquinones, isopentenyl adenine and farnesol. HMG-CoA reductase converts 3-hydroxy-3-methyld-glutaryl CoA (HMG-CoA) to mevalonate.

HMG-CoA reductase inhibitors, or statins, enhance the production of osteoblasts, the cells that produce new bone and enhance osteoblast differentiation. See S. E. Harris, et al., (1995) Mol. Cell. Differ. 3, 137; see also G. Mundy, et al., Science, (1999) 286, 1946. In particular, statins have been known to promote BMP production systematically or in fracture sites. See U.S. Pat. Nos. 6,080,779, 6,376,476, and 6,022,887.

Examples of the HMG-CoA reductase inhibitors of the present invention include, but not limited to, lovastatin, pravastatin, velostatin, simvastatin, fluvastatin, cerivastatin, mevastatin, dalvastatin, fluindostatin, atorvastatin, or a prodrug thereof, a pharmaceutically acceptable salt of any such HMG-CoA reductase inhibitors, or prodrug thereof. Preferable salts include calcium and/or phosphate salts. In a preferred embodiment, the HMG-CoA reductase inhibitor is simvastatin or simvastatin calcium. In another preferred embodiment, the HMG-CoA reductase inhibitor is lovastatin or lovastain calcium.

HMG-CoA reductase inhibitors may be readily prepared by processes known in the chemical arts. Mevastatin, lovastatin, pravastatin, velostatin, simvastatin, fluvastatin, cerivastatin and mevastatin, dalvastatin and fluindostatin can be made in accordance with the process set forth in U.S. Pat. Nos. 3,983,140, 4,231,938, 4,346,227, 4,448,784, 4,450, 171, 4,739,073, 5,177,080, 5,177,080, European Patent Application No. 738,510 A2 and European Patent Application No. 363,934 A1, respectively, which are all incorporated herein by reference in their entirety. Furthermore, atorvastatin can be prepared as described in U.S. Pat. No. 4,681,893, which is incorporated in its entirety by reference. The hemicalcium salt of atorvastatin, also known as Lipitor™, can be prepared as described in U.S. Pat. No. 5,273, 995, which is incorporated in its entirety by reference. Other pharmaceutically-acceptable cationic salts of atorvastatin may be readily prepared by reacting the free acid form of atorvastatin with an appropriate base, usually one equivalent, in a co-solvent.

The present invention involves the use of such compounds to promote non-anatomic bone growth, or bone growth in a site that does not normally grow bone (e.g., aid in the fusion of two or more bone surfaces or augment growth of a bone surface). Bone fusion is effective in treatment of, for example, post-traumatic, degenerative and inflammatory arthritis conditions.

In one embodiment, HMG-CoA reductase inhibitors are used to stimulate non-anatomic bone growth at, near, surrounding or between any vertebra or vertebra structures including, but not limited to, the pedicles, dorsal spinal elements, traverse processes, accessory processes and superior articular processes, mamillary processes, laminae, vertebral bodies or combination thereof.

In another embodiment, HMG-CoA reductase inhibitors are used to enhance non-anatomic bone growth at, near, surrounding or between bones of the feet, including but not limited to, the tarsals, metatarsals, phalanges, tibia, fibula, calcaneous, talus, etc., or a combination thereof.

In a further example, the present invention envisions the administration of HMG-CoA reductase inhibitors to a site at, near, surrounding or between facial bones, including but not limited to, the mandible, maxilla, lacrimal, vomer, frontal bone, nasal bone, palantine, inferior concha, hyoid, zygoma, or any combination thereof.

Administration of the HMG-CoA reductase inhibitor can be via any mode, which delivers the HMG-CoA reductase inhibitor locally to the site of bone fusion or non-anatomic bone growth is desired. In preferred embodiments, the HMG-CoA reductase inhibitor is administered directly to a given site. Direct administration can be made in surgery when the wound is open or using an injection or other means to reach a desired site without surgery.

Preparation for direct application can comprise of aerosol sprays, solutions, lotions, gels ointments, preferably in pharmaceutically acceptable vehicle. Such vehicles include aliphatic alcohols, polyglycols, glycerol, polyethylene, glycol, esters of fatty acids, oils (e.g., arachis oil), bone-wax, polymeric bone cements, bone sealants, and silicones.

Alternatively, local application can be achieved by applying the compounds herein into or onto a suitable carrier or diluent, or incorporating it into solid or semi-solid implants (non-compressible carriers) that are conventionally used in orthopedic surgery, such as, for example, dacron-mesh, gel-foam and kiel bone, or prostheses. In a preferred embodiment, the HMG-CoA reductase inhibitor is administered in combination with a compressible carrier such as a porous, open cell matrix formed from collagen fibers coated with resorbable hydroxyapatite.

In any of the embodiments herein, a time-release formulations of HMG-CoA reductase inhibitor may be used. A time-release formulation preferably comprises of hydrogel. A time-release formulation can be designed for short term or long term release. A short term time-release formulation can be designed to release a total of 0.1–1 g of HMG-CoA reductase inhibitor per day, or more preferably 0.2–0.8 g of HMG-CoA reductase inhibitor per day, or more preferably 0.3–0.6 g of HMG-CoA reductase inhibitor per day, or more preferably 0.4–0.5 g of HMG-CoA reductase inhibitor per day. Short term release formulations can last a few days or a week.

A long term time-release formulation can be designed to release HMG-CoA inhibitor for a week or longer. In a preferred embodiment, a formulation for long term time-release can be designed to release a total of 0.01–0.5 g of HMG-CoA reductase inhibitor per day, or more preferably 0.05–0.4 g of HMG-CoA reductase inhibitor per day, or more preferably 0.07–0.3 g of HMG-CoA reductase inhibitor per day, or more preferably 0.07–0.2 g of HMG-CoA reductase inhibitor per day.

In any of the embodiments herein, a preparation, vehicle, implant or carrier may further support other compounds such as, for example, antioxidants, growth factors, antibiotics, anti-inflammatories, immunosuppressors, preservative, pain medication, other therapeutics, and excipient agents.

Examples of growth factors that may be administered in addition to the HMG-CoA reductase inhibitor include, but are not limited to, epidermal growth factor (EGF), transforming growth factor-alpha (TGF-.alpha.), transforming growth factor-beta (TGF-.beta.), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

The HMG-CoA reductase inhibitor may also be provided in a time-release drug delivery system, for example via a hydrogel, polymer membrane, or coating. Methods of delivering the compounds using a time-release system include those described in PCT publication WO 93/20859, incorporated herein by reference. In other embodiments, the HMG-CoA reductase inhibitor is administered percutaneously within a supporting compound at the site where bone fusion is desired. Such embodiment promotes BMP production without necessitating surgery.

In one example, a procedure involves exposing the lamina and transverse processes, decorticating bone, and placing the carrier with HMG-CoA reductase inhibitor in the exposed area. Furthermore, the carrier may employ covalent or divalent bonding to the HMG-CoA reductase inhibitor. The carrier may also be used in conjunction or as a spinal fusion device such as a cage.

The amount of HMG CoA reductase inhibitor administered depends on the procedure, type of HMG CoA reductase inhibitor used, severity of the condition, age of patient, and/or cardiac health of the patient. In one embodiment, 0.1 to 1 grams of HMG-CoA reductase inhibitor are administered per site per treatment. More preferably, 0.2 to 0.5 grams of HMG-CoA reductase inhibitor is administered per site per treatment. More preferably, 0.25 to 0.3 grams of HMG-CoA reductase inhibitor are administered per site per treatment. Treatment may be repeated several times (e.g., twice, thrice, four times) or routinely (e.g., daily, weekly, monthly) as determined for example by X-ray or other indication into a given site.

The amount and timing of compounds administered to a patient will, of course, be dependent on the subject being treated, on the severity of the affliction, on the manner of administration and on the judgment of the prescribing physician. Thus, because of patient-to-patient variability, the dosages given herein are a guideline and the physician may titrate doses of the compound to achieve the treatment (e.g., bone mass augmentation) that the physician considers appropriate for the patient. In considering the degree of treatment desired, the physician must balance a variety of factors such as bone mass starting level, age of the patient, presence of preexisting disease, as well as presence of other diseases (e.g., cardiovascular disease).

Methods of preparing various pharmaceutical compositions using carriers with a certain amount of active ingredients are known, or will be apparent in light of this disclosure, to those skilled in the art. For examples of methods of preparing pharmaceutical compositions, see Remington: The Science and Practice of Pharmacy, Mack Publishing Company, Easton, Pa., 19th Edition (1995).

The present invention can be used during surgery or revision surgery. A common problem in spine fusion is that it is non-successful and results in non-union. Non-union is particularly difficult to treat and administering an HMG-CoA reductase inhibitor during revision surgery can increase the likelihood of fusion. Furthermore, the method and instrumentations herein may be used for both open and minimally invasive surgical procedures including endoscopic and arthroscopic procedures wherein access to the surgical site is achieved through a cannula or small incision.

Aside from spinal fusion, other procedures, for example, in podiatry, dentistry and facial reconstruction, which currently rely on wires, plates and screws may also benefit from the growth of non-anatomic bone. These procedures include arthrodesis for failed ankle arthoplasty and/or for the first metatarsophalangeal joint (see Jones, S. et al., The Foot, (1999) 9, 142–144; see also Fadel, G. E., The Foot (2002) 12, 88–96); subtalar fusion surgery for patients who failed closed or open treatment of a displaced intra-articular calcaneal fracture (see Csizy, M., J. Ortopaedic Trauma, (2003) 17(2), 106–112); fixation of bimaxillary osteotomized segments (see Edwards, R., J. Oral Marillofac. Surg. (2001) 59:271–276); and cranial vault remodeling (see Fearon, J A, Plastic and Reconstructive Surgery, (2003) 111(1), 27–38).

It should be noted that while most contemplated applications of the present invention are concerned with use in humans, the products and methods herein can be used in non-human animals as well.

FIG. 1 illustrates a $2^{nd}$ lumbar vertebra as an example vertebra fused using the present invention. The vertebra comprises a vertebral body 10 with first and second pedicles 12 and 14 extending posteriorly therefrom. The pedicles 12 and 14 are strong, cylindrical, anatomic bridges between the dorsal spinal elements and the vertebral body 10. The dorsal spinal elements comprise generally symmetrical transverse processes 16 and 18, accessory processes 20 and 22, superior articular processes 24 and 26, mamillary processes 28 and 30, and laminae 32 and 34 which eventually meet at a single spinous process 36.

Figure 2:
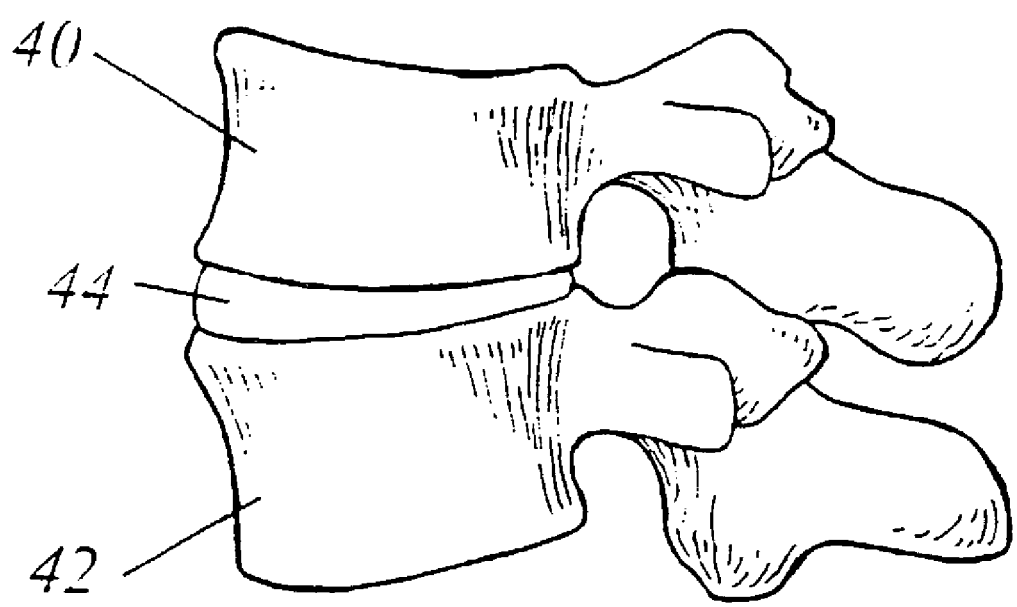
FIG. 2 is a lateral view of the cervical or lumbar spine.

FIG. 2 depicts a lateral view of the cervical or lumbar spine. Top and bottom vertebral bodies 40 and 42 are separated by an intervertebral disc 44. In spinal fusion, bone growth by the top and bottom vertebra is promoted in order to cause the top and bottom vertebra to fuse. The fusion typically involves placement of a bone graft, cage, instrumentation, or other implant, at a site where fusion is desired. The body engages in a natural bone growth healing process. The bone growth results in growth of the bone graft such that the top and bottom vertebrae are fused and motion therebetween is prevented. The bone growth may be between the vertebral bodies, through the intervertebral disc space, between the transverse processes, between the laminae, or between a combination thereof.

In accordance with the present invention, an HMG-CoA reductase inhibitor is placed adjacent to the vertebrae as desired. This may be, for example, adjacent to the transverse process, in the intervertebral disc space, or overlying the lamina. A preferred embodiment involves administering approximately 0.1–1 g, or more preferably 0.2–0.5 g, of the HMG-CoA reductase inhibitor, for example, lovastatin to a site per treatment. Local administration of the HMG-CoA reductase inhibitor is preferred and maybe performed by conventional methods such as injection at the spinal fusion site, topical application to the site, or time release administration.

Figure 3:
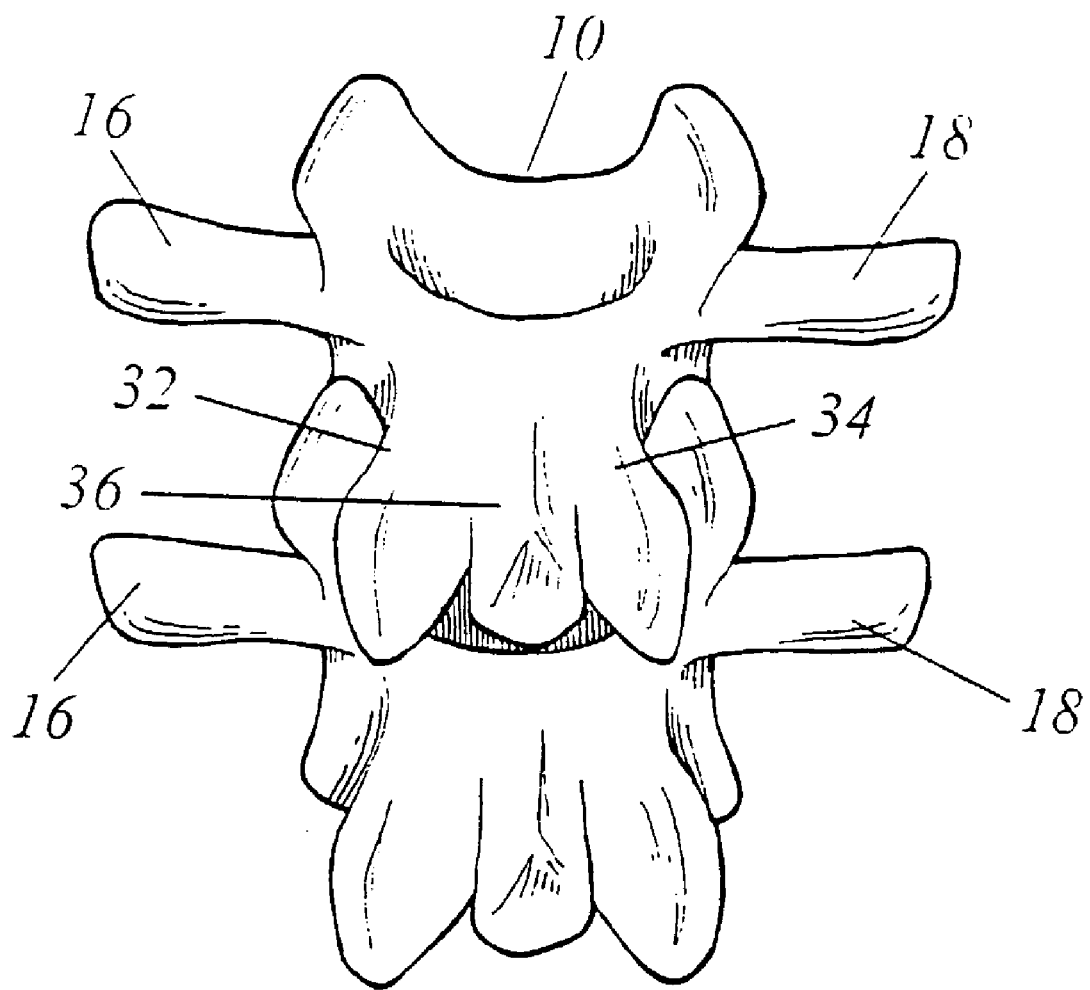
FIG. 3 is a posterior view of the $3^{rd}$ and $4^{th}$ lumbar vertebrae.

FIG. 3 shows a posterior view of the third and fourth lumbar vertebrae. From this perspective, the transverse processes 16 and 18 are more clear. In spinal fusion surgery, the vertebrae may be joined at the transverse processes 16 and 18 of adjacent vertebrae. One possible procedure in accordance with the present invention involves exposing the lamina 32 and 34 and transverse processes 16 and 18, decorticating the bone, and placing a carrier with HMG-CoA reductase inhibitor in the exposed area.

Figure 4:
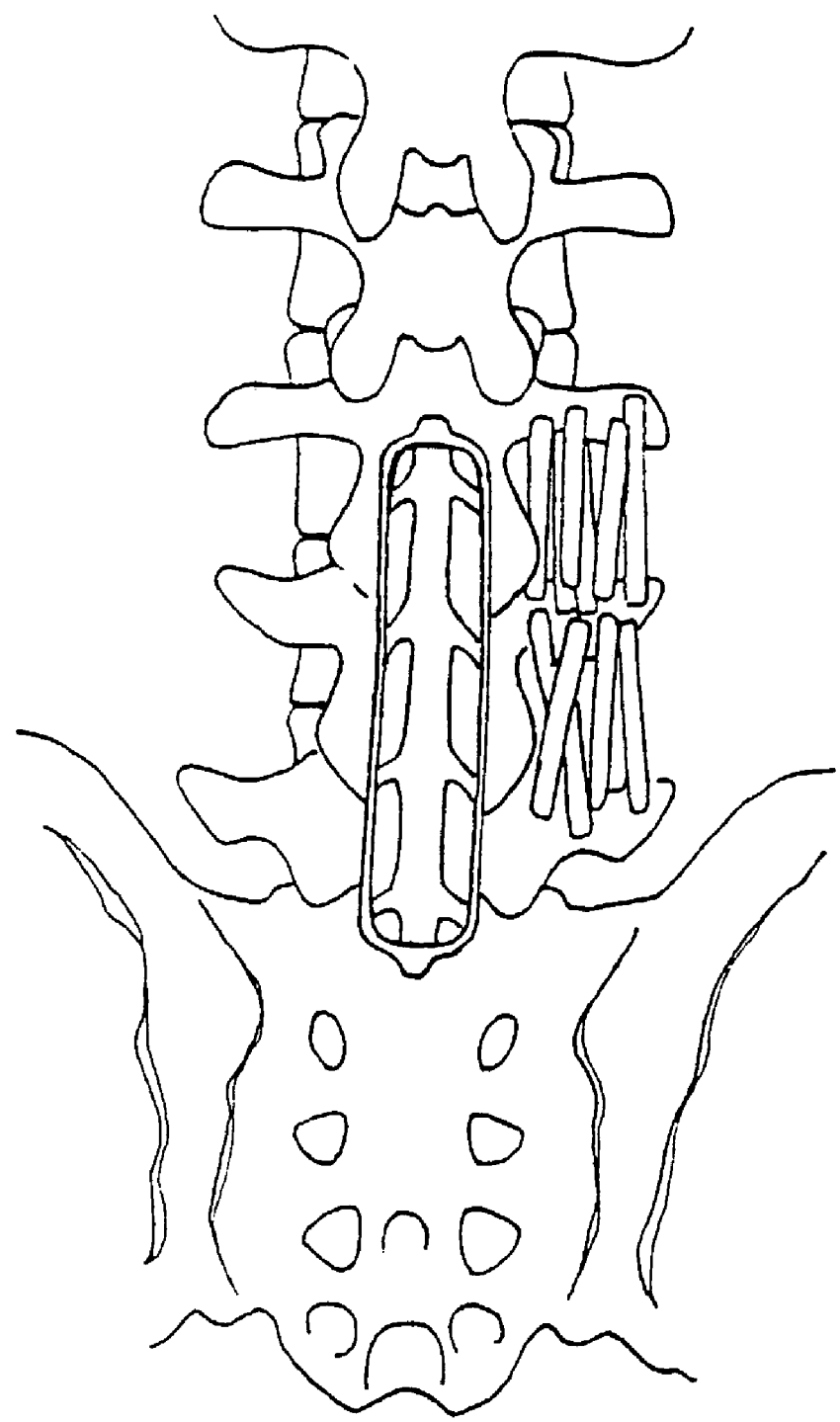
FIG. 4 is a dorsal view of a dorsolateral fusion after total laminectomy.

Preferably, local administration is performed by applying the HMG-CoA reductase inhibitor to a carrier and placing the carrier at the spinal fusion site. FIG. 4 depicts a dorsolateral fusion after total laminectomy. The fusion bed involves the dorsal aspect of the transverse process, the facet joint, and the pars interarticularis. In one embodiment of the current invention, an HMG-CoA reductase inhibitor is applied to the carrier and the carrier is placed along the decorticated transverse processes. Antibiotics, other drugs, or pain medications may be supported by the carrier. The HMG-CoA reductase inhibitor may also be provided in a time release drug delivery system, for example via a hydrogel, polymer membrane, or coating.

Figure 5:
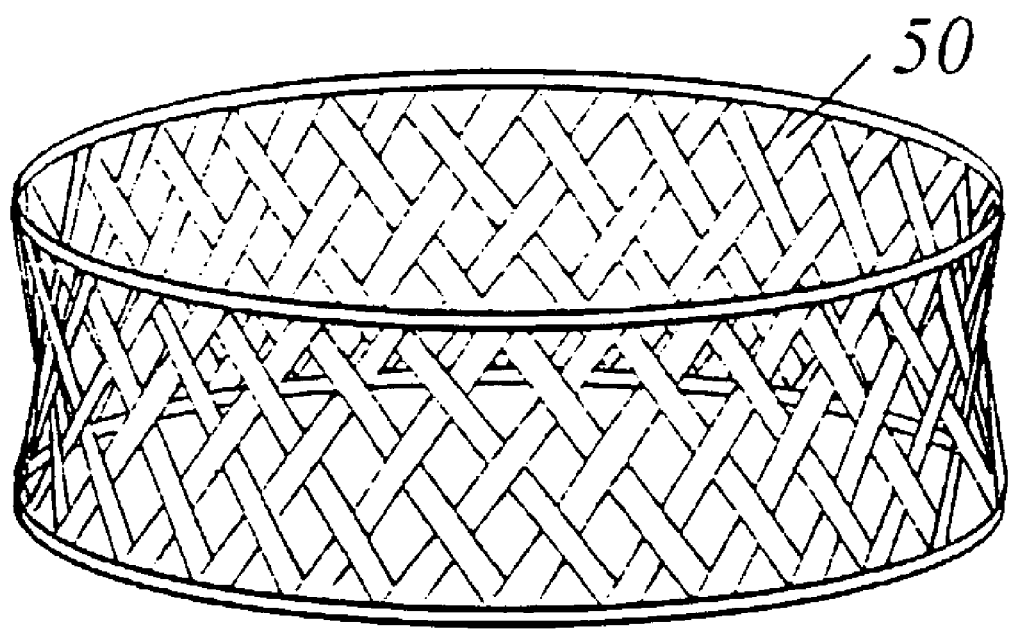
FIG. 5 is a perspective view of a carrier for use with one embodiment of the present invention.

In a preferred embodiment, the HMG-CoA reductase inhibitor is administered to the site via a carrier, for example, a porous, open cell matrix formed from collagen fibers coated with resorbable hydroxyapatite. FIG. 5 illustrates a suitable carrier 50. The carrier 50 may comprise a collagen or cellular matrix. Further, the carrier 50 may employ covalent or divalent bonding to the HMG-CoA reductase inhibitor. The carrier 50 may also be used in conjunction with or as a spinal fusion device such as a cage.

Figure 6:
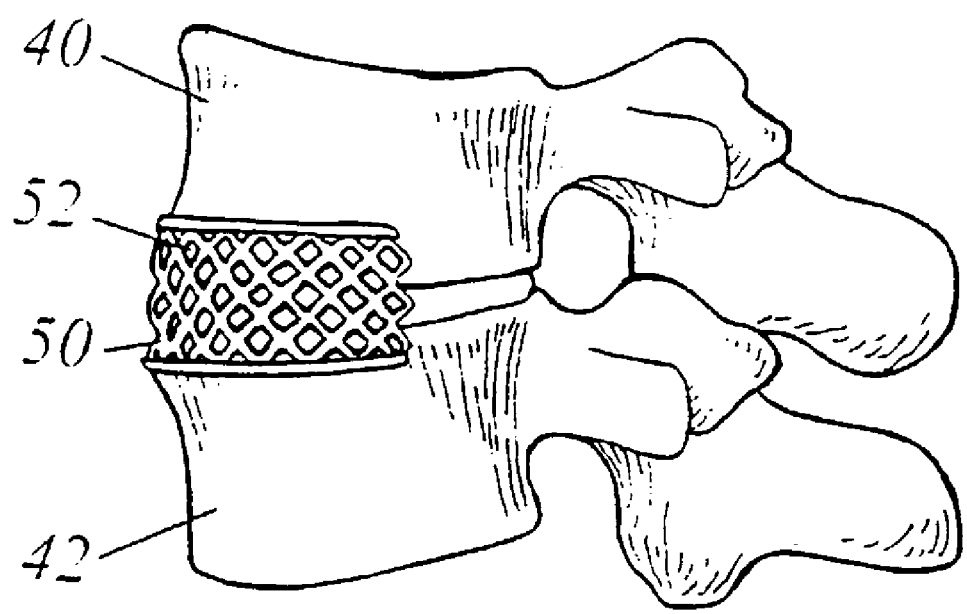
FIG. 6 is a perspective view of a carrier packed in place for spinal fusion in one embodiment of the present invention.

As seen in FIG. 6, the carrier 50 may be packed with HMG-CoA reductase inhibitor 52 and placed in the intervertebral disc space to promote fusion of the vertebra through that space. The HMG-CoA reductase inhibitor is carried to the site by the carrier. Most preferably, the HMG-CoA reductase inhibitor 52 is delivered to the site in conjunction with spinal surgery instrumentation. In a preferred embodiment, the HMG-CoA reductase inhibitor fills the pores of a porous spinal surgery instrumentation device. Thus, the carrier is essentially soaked with HMG-CoA reductase inhibitor that enables a high volume of the HMG-CoA reductase inhibitor to be released. The carrier may further be coated with a time-release film.

Figure 7:
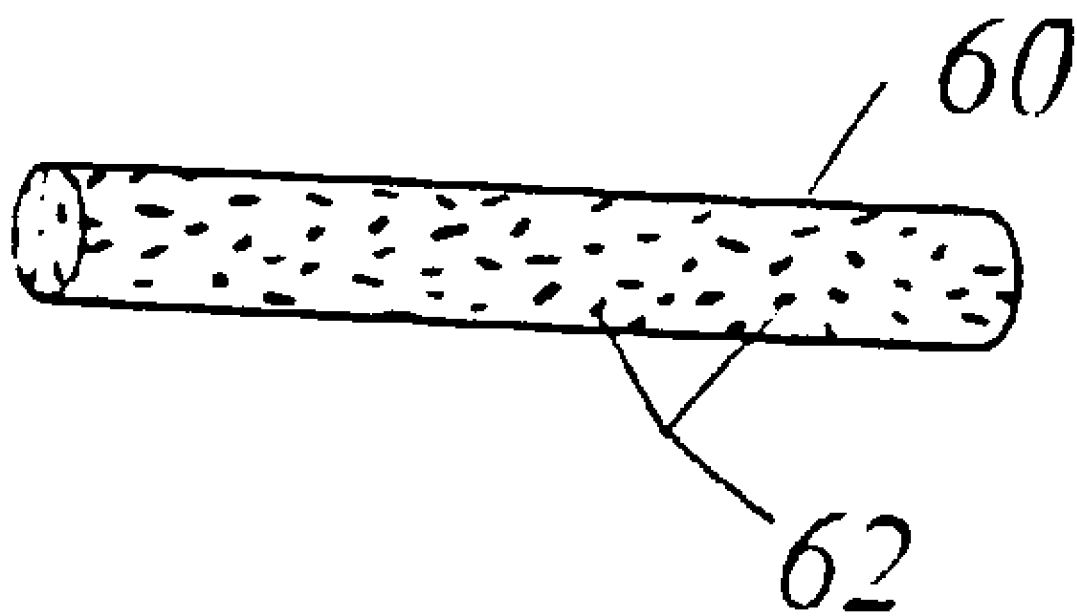
FIG. 7 is a perspective view of an implantation stick in accordance with one embodiment of the present invention.

A further embodiment of the invention includes delivering the HMG-CoA reductase inhibitor to the spinal fusion site with a noncompressible delivery vehicle. The noncompressible delivery vehicle enables a larger volume of bone formation and therefore increases load-bearing capacity of the fusion site. FIG. 7 illustrates a non-compressible delivery vehicle in the form of an implantation stick 60. The stick 60 can be hollow or porous and includes a plurality of openings 62. The implantation stick 60 may be packed with an HMG-CoA reductase inhibitor in a time-release manner, or with hydroxy appetite.

Figure 8:
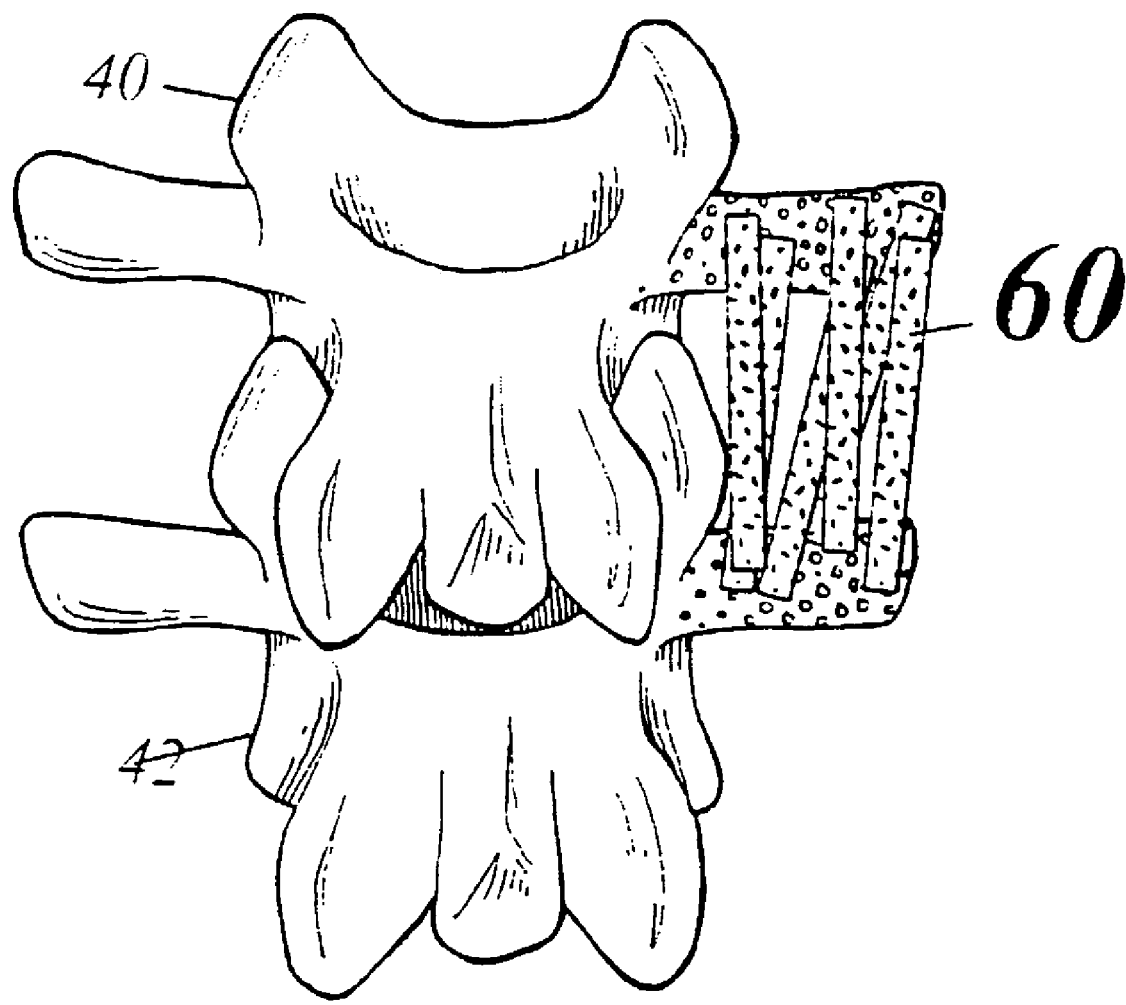
FIG. 8 is a perspective view of posterior lumbar lateral fusion according to one embodiment of the present invention using a plurality of implantation sticks.

FIG. 8 illustrates posterior lumbar lateral fusion according to one embodiment of the present invention using a plurality of implantation sticks 60. In accordance with the present invention, the lamina and transverse process are exposed, bone decorticated, and the carrier with HMG-CoA reductase inhibitor is placed in the exposed area. In the embodiment of FIG. 8, the carrier comprises a plurality of implantation sticks 60 that are placed approximately on the adjacent decorticated lamina and transverse processes bridging the gap between the transverse process of an upper vertebra 40 and the transverse process of a lower vertebra 42. The noncompressible delivery vehicle, for example, the implantation sticks 60, retains a volume between the vertebrae for bone growth. The non-compressible delivery vehicle is packed with an HMG-CoA reductase inhibitor to promote bone growth along the vehicle.

The present invention may involve any suitable instrumentation. For example, a screw may be employed, the screw having an HMG-CoA reductase inhibitor carried thereupon. The screw may comprise a porous material, the HMG-CoA reductase inhibitor being soaked in the pores. Alternately, the screw may be cannulated with the HMG-CoA reductase inhibitor being provided in the hollow opening. Such screws maybe used in odontoid screw fixation or c1–c2 transarticular screw fixations. The screw may traverse the fracture site or the joint to produce fusion at the level of the joint.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

EXAMPLES

Example 1

Twelve male Sprague Dawley rats, each weighing approximately 500 grams were selected. Each rat underwent anesthesia with Nembutal (50 mg/kg i.p.). Incision over two regions, the thoracic and lumbar, of the spine in each animal were made. Each incision allowed for the exposure of spinous processes and lamina of at east 2 levels per region. Decortication was carried out at each thoracic and lumbar region using a high-speed drill. Over the decorticated levels, nothing, gelmatrix, gelmatrix plus 8 mg lovastatin or gelmatrix plus 16 mg lovastatin were added. 8 mg I.M. of antibiotic Cefazolin™ was subcutaneously administered to each rat.

For the purposes of analysis, the rats were divided into three groups. Group A consisting of rats 1–4 was treated with nothing or gelmatrix. Group B consisting of rats 5–8 was treated with gelmatrix and 8 mg of lovastatin. And, group C consisting of rats 9–12 was treated with gelmatrix and 16 mg of lovastatin. The following is a summary of the data:

TABLE 1

| Rat | wt (g) | Spinal Region | Treatment |
|-----|--------|---------------|-----------|
| 1   | 475    | T             | Nothing   |
|     |        | L             | Gel       |
| 2   | 536    | T             | Gel       |
|     |        | L             | Nothing   |
| 3   | 633    | T             | Nothing   |
|     |        | L             | Gel       |
| 4   | 499    | T             | Gel       |
|     |        | L             | Nothing   |
| 5   | 542    | T             | Gel       |
|     |        | L             | Gel + 8 mg |
| 6   | 480    | T             | Gel + 8 mg |
|     |        | L             | Gel       |
| 7   | 504    | T             | Gel       |
|     |        | L             | Gel + 8 mg |
| 8   | 477    | T             | Gel + 8 mg |
|     |        | L             | Gel       |

TABLE 1-continued

| Rat | wt (g) | Spinal Region | Treatment |
|-----|--------|---------------|-----------|
| 9   | 483    | T             | Gel       |
|     |        | L             | Gel + 16 mg |
| 10  | 415    | T             | Gel + 16 mg |
|     |        | L             | Gel       |
| 11  | 440    | T             | Gel       |
|     |        | L             | Gel + 16 mg |
| 12  | 459    | T             | Gel + 16 mg |
|     |        | L             | Gel       |

Figure 11:
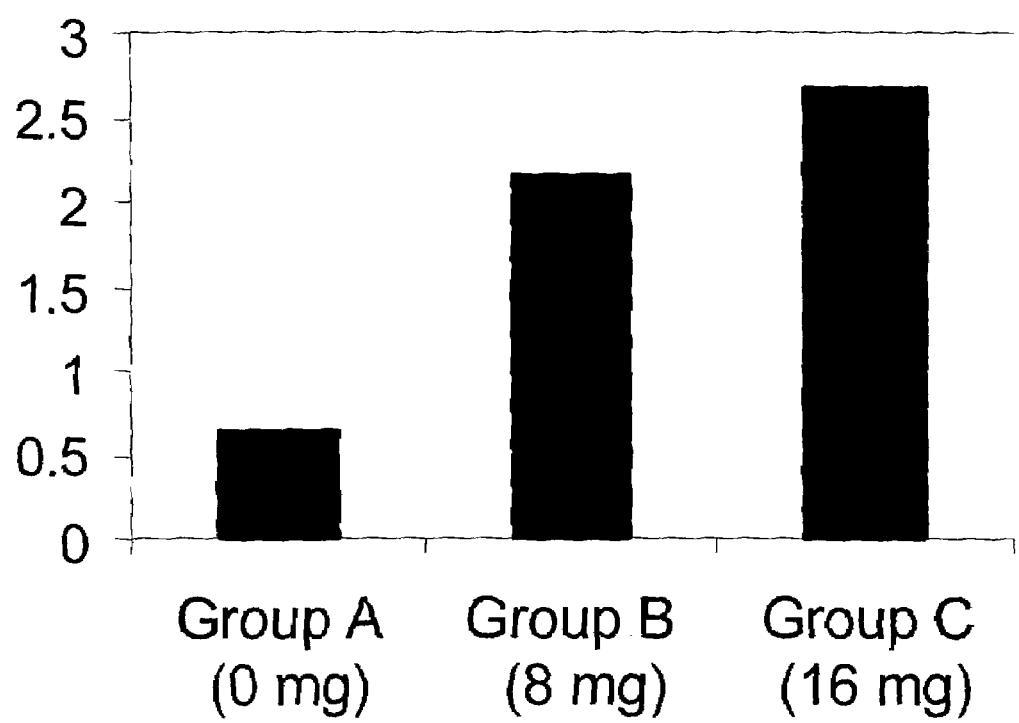
FIG. 11 illustrates palpation score of rats receiving HMG-CoA reductase inhibitor treatment and controls.

After en bloc removal, two observers manually palpated the spine of each rat in a blinded fashion. Palpation was made by flexion and extension at the level of the arthrodesis and at the adjacent levels proximally and distally. This method of evaluation has previously been shown to be more accurate than plain radiographs and to correlate closely with biomechanical test data. Each motion segment was graded on a qualitative scale (0–3) based on the strength of the fusion. A solid fusion having no motion was given a score of 3. A score of 1 or 2 was given to segments that had more restricted motion than the negative control. No fusion was scored as a 0. A summary of the palpitation scores given to each group of rats is illustrated in FIG. 11.

Results indicated that seventy five percent of the rats treated with lovastatin had a stronger fusion at the treated region than rats not treated. Furthermore, the fusion grades given to treated rats appeared to be dose dependent.

Example 2

Figure 9:
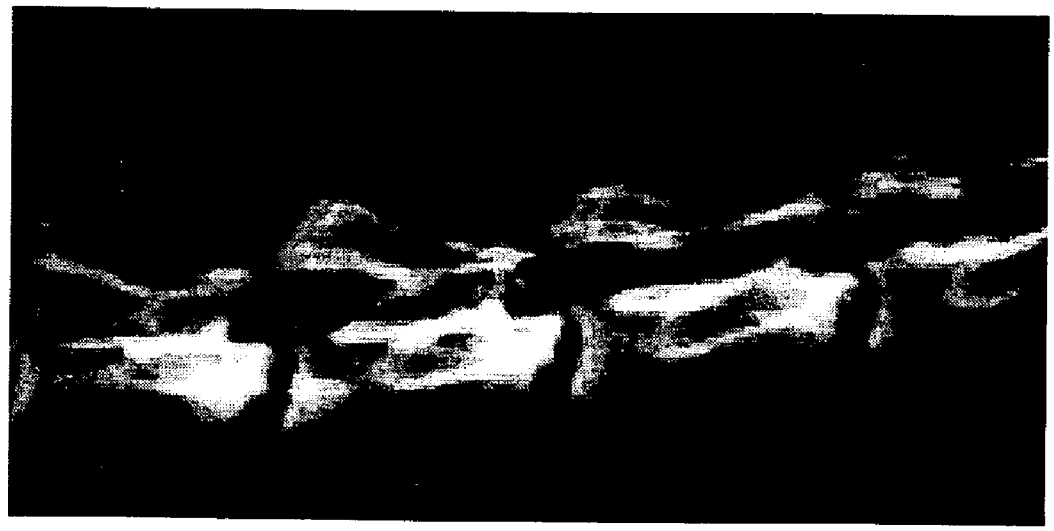
FIG. 9 illustrates a control rat.
Figure 10:
FIG. 10 illustrates a rat that was treated with an HMG-CoA reductase inhibitor.

Spines of rats treated and untreated with HMG-CoA reductase inhibitor were fixed and processed for pathology analysis by light microscopy and radiographic analysis. The X-ray of the spine of a rat that was not treated with HMG-CoA reductase inhibitor is illustrated in FIG. 9. Rats treated with HMG-CoA reductase inhibitor appear to have an augmented spinal fusion in a dose dependent manner as is illustrated in FIG. 10.

What is claimed is:

1. A method for enhancing non-anatomic bone formation in a site, the method comprising the steps of administering an HMG-CoA reductase inhibitor to the site.

2. The method of claim 1 wherein the HMG-CoA reductase inhibitor is lovastatin, or any salt, prodrug or derivative thereof.

3. The method of claim 1, wherein the HMG-CoA reductase inhibitor is pravastatin, or any salt, prodrug or derivative thereof.

4. The method of claim 1 wherein the HMG-CoA reductase inhibitor is simvastatin, or any salt, prodrug or derivative thereof.

5. The method of claim 1 wherein the HMG-CoA reductase inhibitor is atorvastatin, or any salt, prodrug or derivative thereof.

6. The method of claim 1 wherein the HMG-CoA reductase inhibitor is dalvastatin, or any salt, prodrug or derivative thereof.

7. The method of claim 1 wherein the HMG-CoA reductase inhibitor is fluindostatin, or any salt, prodrug or derivative thereof.

8. The method of claim 1 wherein the HMG-CoA reductase inhibitor is cerivastatin, or any salt, prodrug or derivative thereof.

9. The method of claim 1 wherein the HMG-CoA reductase inhibitor is mevastatin, or any salt, prodrug or derivative thereof.

10. The method of claim 1 wherein the HMG-CoA reductase inhibitor is velostatin, or any salt, prodrug or derivative thereof.

11. The method of claim 1 wherein the HMG-CoA reductase inhibitor is administered using a carrier.

12. The method of claim 11 wherein the carrier is a non-compressible carrier.

13. The method of claim 11, wherein the non-compressible carrier is coated with the HMG-CoA reductase inhibitor.

14. The method of claim 11 wherein the carrier is a compressible carrier.

15. The method of claim 14 wherein the compressible carrier is a hydrogel.

16. The method of claim 11 wherein the carrier is an open cell matrix.

17. The method of claim 16 wherein the open cell matrix is formed from collagen fibers.

18. The method of claim 17 wherein the collagen fibers are coated with resorbable hydroxyapatite.

19. The method of claim 18 wherein the hydroxyapatite further comprises calcium.

20. The method of claim 11 wherein the carrier further comprises another compound.

21. The method of claim 20 wherein the compound is an antibiotic.

22. The method of claim 20 wherein the compound is a pain medication.

23. The method of claim 20 wherein the compound is an antioxidant.

24. The method of claim 12 wherein the non-compressible delivery vehicle comprises at least one implantation stick for application to the site such that the implantation stick extends lengthwise between the upper and lower vertebrae.

25. The method of claim 1 wherein the step of administering the HMG-CoA reductase inhibitor includes the step of applying the HMG-CoA reductase inhibitor with a time release drug delivery system.

26. The method of claim 25 wherein the time release drug delivery system comprises a hydrogel.

27. The method of claim 1 wherein the step of administering the HMG-CoA reductase inhibitor includes administering 0.1–1 gram of the HMG-CoA reductase inhibitor to the site per treatment.

28. The method of claim 27 wherein treatment is repeated 3–5 times.

29. A method for promoting spinal fusion, the method comprising the steps of:
    exposing an upper vertebra and a lower vertebra;
    identifying a site for fusion between the upper and the lower vertebra;
    exposing a bony surface on each of the upper and the lower vertebra at the site for fusion;
    applying an HMG-CoA reductase inhibitor to a carrier;
    applying the carrier to one of the exposed bony surfaces at the site.

30. The method of claim 29 wherein the spinal fusion is selected from the group consisting of a posterolateral gutter fusion, a posterior lumbar interbody fusion, an anterior lumbar interbody fusion, an anterior/posterior spinal fusion, a cervical fusion, a thoracic fusion and an interlaminar fusion.

31. The method of claim 30 wherein the spinal fusion is the posterolateral gutter fusion.

32. The method of claim 31 wherein the HMG-CoA reductase inhibitor is place in a posterolateral portion of a spine on a first and a second transverse processes.

33. The method of claim 30 wherein the spinal fusion is the posterior lumbar interbody fusion.

34. The method of claim 31 wherein the HMG-CoA reductase inhibitor is administered directly into a disc space.

35. The method of claim 30 wherein the spinal fusion is the anterior lumbar interbody fusion.

36. The method of claim 35 wherein the HMG-CoA reductase inhibitor is administered directly into a disc space.

37. The method of claim 30 wherein the spinal fusion is the anterior/posterior spinal fusion.

38. The method of claim 30 wherein the spinal fusion is the cervical fusion.

39. The method of claim 30 wherein the spinal fusion is the thoracic fusion or interlaminar fusion.

40. The method of claim 29 wherein the carrier is a non-compressible delivery vehicle.

41. The method of claim 30 wherein the non-compressible delivery vehicle comprises of at least one implantation stick for application to the site such that the implantation stick extends lengthwise between the upper and lower vertebrae.

42. A method of promoting non-anatomical bone growth between two bony surfaces, the method comprising the steps of:
    identifying a site between two bony surfaces where bone growth is desired but does not naturally occur;
    exposing bone at each of the two bony surfaces;
    applying an HMG-CoA reductase inhibitor to at least one of the bony surfaces.

43. The method of claim 42 wherein the step of administering the HMG-CoA reductase inhibitor further includes the steps of providing the HMG-CoA reductase inhibitor on a carrier and applying the carrier to the site.

44. The method of claim 43 wherein the carrier is a non-compressible delivery vehicle.

45. The method of claim 44 wherein the non-compressible delivery vehicle comprises of steel, ceramic, titanium, coral or hydroxyapatite.

46. A method for fixation of maxillary and mandibular osteotomies comprising:
    identifying a site for fusion between a maxillary bone and a mandibular bone;
    exposing a bony surface at each of the two bones;
    applying an HMG-CoA reductase inhibitor to at least one of the bony surfaces.

47. The method of claim 46 wherein the HMG-CoA reductase inhibitor is on or in a carrier.

48. The method of claim 47 wherein the carrier is a non-compressible implant.

49. The method of claim 47 wherein the carrier is an open cell matrix.

50. The method of claim 49 wherein the matrix is composed of collagen.

51. The method of claim 47 wherein the carrier is a timed release carrier.

52. A carrier for enhancing bone formation wherein said carrier comprises an HMG-CoA reductase inhibitor.

53. The carrier of claim 52 further wherein said carrier is an open cell matrix.

54. The carrier of claim 53 wherein the matrix is formed of collagen.

55. The carrier of claim 52 wherein the carrier further comprises an antibiotic, a pain medication, a growth hormone or a combination thereof.

56. The carrier of claim 52 wherein said carrier is non-compressible.

57. The carrier of claim 56 wherein the carrier comprises of steel, ceramic, titanium, coral or hydroxyapatite.

* * * * *